(12) United States Patent
Cao et al.

(10) Patent No.: US 11,950,796 B2
(45) Date of Patent: Apr. 9, 2024

(54) ULTRASONIC BONE SCALPEL BIT AND ROBOT-ASSISTED ULTRASONIC BONE POWER SYSTEM USING SAME

(71) Applicant: BEIJING SMTP TECHNOLOGY CO., LTD., Beijing (CN)

(72) Inventors: Qun Cao, Beijing (CN); Songtao Zhan, Beijing (CN); Zhiling Dai, Beijing (CN)

(73) Assignee: BEIJING SMTP TECHNOLOGY CO., LTD., Beijing (CN)

( * ) Notice: Subject to any disclaimer, the term of this patent is extended or adjusted under 35 U.S.C. 154(b) by 793 days.

(21) Appl. No.: 16/934,528

(22) Filed: Jul. 21, 2020

(65) Prior Publication Data

US 2021/0030435 A1 Feb. 4, 2021

(30) Foreign Application Priority Data

Jul. 31, 2019 (CN) .......................... 201910700526.3

(51) Int. Cl.
*A61B 17/32* (2006.01)
*A61B 17/16* (2006.01)
*A61B 34/30* (2016.01)

(52) U.S. Cl.
CPC .. *A61B 17/320068* (2013.01); *A61B 17/1628* (2013.01); *A61B 17/1662* (2013.01);
(Continued)

(58) Field of Classification Search
CPC ........... A61B 17/320068; A61B 2017/320077; A61B 17/142; A61B 17/144; A61B 17/1659
See application file for complete search history.

(56) References Cited

U.S. PATENT DOCUMENTS

| 5,935,143 A | 8/1999 | Hood |
| 6,379,371 B1 | 4/2002 | Novak et al. |

(Continued)

FOREIGN PATENT DOCUMENTS

| CN | 203354612 U | 12/2013 |
| CN | 107320151 A | 11/2017 |

(Continued)

OTHER PUBLICATIONS

Office Action cited in corresponding Japanese Patent Application No. 2020-128967 dated Jun. 29, 2021 (10 pages).

(Continued)

*Primary Examiner* — Julian W Woo
(74) *Attorney, Agent, or Firm* — Osha Bergman Watanabe & Burton LLP

(57) ABSTRACT

An ultrasonic bone scalpel bit includes a scalpel bit end portion located at a distal end of the scalpel bit, the scalpel bit end portion being formed to have a flat shape and provided with a cutting portion. The cutting portion includes a distal end portion, a first side portion and a second side portion, the first side portion and the second side portion being symmetrically arranged relative to a longitudinal axis of the scalpel bit end portion in a width direction of the scalpel bit end portion. The cutting portion further includes a plurality of protrusions formed near the distal end portion, the plurality of protrusions projecting outward from the first side portion and the second side portion symmetrically relative to the longitudinal axis in the width direction of the scalpel bit end portion.

17 Claims, 7 Drawing Sheets

(52) U.S. Cl.
CPC ...... *A61B 34/30* (2016.02); *A61B 2017/1651* (2013.01); *A61B 2017/320077* (2017.08); *A61B 2017/320084* (2013.01)

(56) References Cited

U.S. PATENT DOCUMENTS

| | | | |
|---|---|---|---|
| 8,323,302 B2* | 12/2012 | Robertson | A61B 17/320068 606/169 |
| 8,888,783 B2* | 11/2014 | Young | A61B 17/16 606/177 |
| 10,016,208 B2* | 7/2018 | Gouery | A61B 17/320068 |
| 10,219,822 B2 | 3/2019 | Voic et al. | |
| 11,406,414 B2* | 8/2022 | Gras | A61B 17/320068 |
| 2009/0326535 A1* | 12/2009 | Blus | A61B 17/142 606/86 R |
| 2010/0057118 A1 | 3/2010 | Dietz | |
| 2012/0095472 A1 | 4/2012 | Young | |
| 2014/0088597 A1* | 3/2014 | Dibart | A61B 17/142 606/79 |
| 2015/0182232 A1 | 7/2015 | Peterson et al. | |
| 2016/0128711 A1 | 5/2016 | Cao et al. | |

FOREIGN PATENT DOCUMENTS

| | | |
|---|---|---|
| CN | 107518929 A | 12/2017 |
| CN | 207707972 U | 8/2018 |
| CN | 208435715 U | 1/2019 |
| CN | 109620415 A | 4/2019 |
| CN | 110313972 A | 10/2019 |
| CN | 210811334 U | 6/2020 |
| JP | 2004512855 A | 4/2004 |
| JP | 2012524586 A | 10/2012 |
| JP | 2017504400 A | 2/2017 |
| WO | 2017211210 A1 | 12/2017 |
| WO | 2018/220515 A1 | 12/2018 |
| WO | 2018228128 A1 | 12/2018 |
| WO | 2019062348 A1 | 4/2019 |

OTHER PUBLICATIONS

Office Action issued in European Application No. 20186157.2; dated Aug. 23, 2022 (5 pages).

International Search Report issued in Application No. PCT/CN2020/099102, dated Sep. 28, 2020 (5 pages).

* cited by examiner

ULTRASONIC BONE SCALPEL BIT AND ROBOT-ASSISTED ULTRASONIC BONE POWER SYSTEM USING SAME

TECHNICAL FIELD

The present disclosure relates to an ultrasonic bone scalpel bit, and in particular to an ultrasonic bone scalpel bit suitable for use by a surgical robot, and a robot-assisted ultrasonic bone power system using the ultrasonic bone scalpel bit.

BACKGROUND ART

In the ultrasonic orthopedic surgery techniques, a transducer is activated or excited at an ultrasonic frequency to convert electric energy into mechanical energy so as to drive a scalpel bit to cut bone tissues. An ultrasonic bone scalpel has the unique advantage of "cutting hard tissues but not cutting soft tissues", greatly enhancing the safety of orthopedic surgery, and has been widely applied to surgical operations at present.

It is a current research hotspot to automatically complete the surgery by means of a surgical robot under the planning of a doctor, as is the same way in the development of orthopedic surgery. Human hands are advantageous in relatively flexible operation, accurate control over the cutting direction and angle, and immediate adjustment according to actual situations, but at the same time also have the disadvantages of low control accuracy on cutting depth and speed, etc., in particular poor control ability in a longitudinal direction. When an ultrasonic bone power system is operated with human hands to cut through a bone, there is a certain risk of causing damage to other tissues under the bone due to an excessive longitudinal force. Therefore, it is necessary to perform orthopedic surgery assisted by a robot to increase the surgical accuracy and further improve the surgical safety.

Existing ultrasonic bone scalpel bits are all invented based on structural characteristics and operation habits of human hands, so most of the scalpel bits are in a shape that is easy to hold, apply force and control by hands, such as of a sheet-shaped structure similar to an ordinary scalpel. Such bits are not developed based on the structure and operation characteristics of surgical robots, and is not suitable for use by a surgical robot. In particular, since surgical robots have defects of relatively inflexible motion and relatively poor flexibility during the operation, using the existing ultrasonic bone scalpel bits suitable for use by human hands is not conductive to take the advantages of surgical robots in terms of force control, repetition accuracy, etc. Moreover, surgical robots have higher requirements on scalpel bits in terms of repeatable operation performance, quick cooling, immediate discharge of bone fragments, etc. Therefore, it is of great significance to design an ultrasonic bone scalpel bit that adapts to the operation characteristics of a surgical robot.

SUMMARY OF THE INVENTION

An object of the present disclosure is to provide an ultrasonic bone scalpel bit, which is designed based on the structure and operation characteristics of surgical robots and thus is suitable for use by a surgical robot.

According to a first aspect of the present disclosure, there is provided an ultrasonic bone scalpel bit, including a scalpel bit end portion located at a distal end of the scalpel bit, the scalpel bit end portion being formed to have a flat shape and provided with a cutting portion wherein the cutting portion includes a distal end portion, a first side portion and a second side portion, the first side portion and the second side portion being symmetrically arranged relative to a longitudinal axis of the scalpel bit end portion in a width direction of the scalpel bit end portion; the cutting portion further includes a plurality of protrusions formed near the distal end portion, the plurality of protrusions projecting outward from the first side portion and the second side portion symmetrically relative to the longitudinal axis in the width direction of the scalpel bit end portion; and a recess which is recessed toward a proximal end of the scalpel bit end portion is formed on the distal end portion.

According to an embodiment, wherein the recess is symmetrically provided relative to the longitudinal axis of the scalpel bit end portion.

According to an embodiment, wherein the recess has a constant or gradient radius of curvature.

According to an embodiment, wherein the plurality of protrusions include a first protrusion and a second protrusion, the first protrusion is located at the junction of the distal end portion and the first side portion, and the second protrusion is located at the junction of the distal end portion and the second side portion.

According to an embodiment, wherein the first protrusion, the recess and the second protrusion are smoothly and consecutively formed.

According to an embodiment, wherein the thickness of at least part of at least one of the distal end portion, the first side portion, the second side portion and the protrusions of the cutting portion is greater than that of a non-cutting portion, which is adjacent to the cutting portion, of the scalpel bit end portion.

According to an embodiment, wherein the thicknesses of the distal end portion, the first side portion, the second side portion and the protrusions of the cutting portion are greater than that of the non-cutting portion, which is adjacent to the cutting portion, of the scalpel bit end portion.

According to an embodiment, wherein at least one of the distal end portion, the first side portion, the second side portion and the protrusions of the cutting portion has a first thickness portion and a second thickness portion which are arranged alternatively and are different in thickness, with the thickness of the first thickness portion being greater than that of the second thickness portion.

According to an embodiment, wherein the thickness of the second thickness portion is greater than that of the non-cutting portion, which is adjacent to the cutting portion, of the scalpel bit end portion.

According to an embodiment, wherein the cutting portion is at least partially provided with a toothed structure and/or a knurled structure.

According to an embodiment, wherein the toothed structure and/or the knurled structure of the cutting portion is provided all over the cutting portion.

According to an embodiment, wherein the protrusions have a hooked, trapezoidal, square, triangular, or circular arc shape or any combination thereof.

According to an embodiment, wherein the scalpel bit end portion of the ultrasonic bone scalpel bit has a flat sheet-shaped structure.

According to an embodiment, wherein the ultrasonic bone scalpel bit is provided with at least one guide groove for guiding liquid to the cutting portion.

According to an embodiment, wherein the at least one guide groove guides the liquid to at least one of the distal end portion, the first side portion, the second side portion and the protrusions of the cutting portion.

According to an embodiment, wherein the ultrasonic bone scalpel bit is formed with at least one through hole that penetrates in a thickness direction of the scalpel bit end portion.

According to an embodiment, wherein the ultrasonic bone scalpel bit is formed with a through hole that extends to the distal end portion in a length direction of the scalpel bit end portion in the scalpel bit end portion.

According to an embodiment, wherein the ultrasonic bone scalpel bit includes a scalpel rod connected to the scalpel bit end portion, and the scalpel bit end portion and the scalpel rod are integrally formed.

According to an embodiment, wherein the distance between the first side portion and the second side portion in a width direction of the scalpel bit end portion decreases toward the distal end portion.

According to an embodiment, wherein the maximum width of the plurality of protrusions in the width direction of the scalpel bit end portion is greater than or equal to that of a tissue contact portion of the ultrasonic bone scalpel bit in the width direction of the scalpel bit end portion.

According to an embodiment, wherein the thickness of the cutting portion is greater than or equal to the maximum thickness of the tissue contact portion of the ultrasonic bone scalpel bit.

According to a second aspect of the present disclosure, there is provided a robot-assisted ultrasonic bone power system, including an ultrasonic bone power system and a robot-assisted surgery system. The ultrasonic bone power system includes: an ultrasonic transducer for converting electric energy into mechanical energy; an ultrasonic bone scalpel for transferring the mechanical energy to a bone to be cut; and the robot-assisted surgery system for assisting in a surgical operation, wherein the ultrasonic bone scalpel has the ultrasonic bone scalpel bit described above.

BRIEF DESCRIPTION OF THE DRAWINGS

Hereinafter, the technical solution of the present disclosure is further described in detail with reference to accompanying drawings and specific embodiments. The drawings exemplarily show the embodiments and constitute part of the specification, and are used to illustrate the exemplary implementations of the embodiments together with the text description of the specification. The embodiments shown are for illustrative purposes only, but do not limit the scope of protection of the claims. Throughout the drawings, same reference numerals refer to same or like elements. In the drawings:

DETAILED DESCRIPTION OF EMBODIMENTS

First of all, it should be noted that the basic structure, functions, and advantages of the ultrasonic bone scalpel bit will be specifically explained below by way of example, but the entire description is for illustration only and should not be construed as limiting the present disclosure. In addition, in the description of the present disclosure, the orientation or position relationship indicated by the terms "upper", "lower", "front", "rear", "left", "right", "top", "inner", "outer", "longitudinal", "transverse", "horizontal", "vertical", "width direction", "length direction", "thickness direction", etc. is based on the orientation or position relationship shown in the accompanying drawings and the specification, which is only for the convenience of the description of the present disclosure and simplification of the description, rather than specifying or implying that the devices or components involved must have a certain orientation or be constructed and operated in a certain orientation, and therefore should not be construed as limiting the present disclosure. Furthermore, the terms "first" and "second" are used for the descriptive purpose only and should not be construed as specifying or implying the relative importance. Furthermore, a "flat shape" means one different from shapes having a relatively large thickness such as "square shape" and "cylindrical shape", and may have a certain thickness; being "flat" means being different from some non-planar structures, such as "arc", and it not required to be absolute flat; and a "distal end" and a "proximal end" are defined relative to the operating mechanism of the ultrasonic bone scalpel, a "distal end" referring to an end close to the scalpel bit and away from the operating mechanism, and a "proximal end" referring to an end close to the operating mechanism and away from the scalpel bit.

The present disclosure will be further described in detail below by way of the specific embodiments and with reference to the accompanying drawings.

Figure 1:
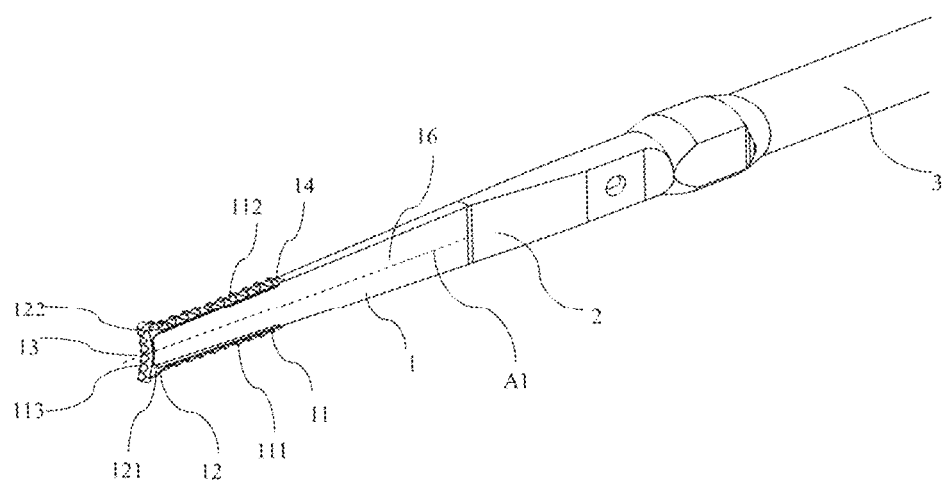
FIG. 1 is a perspective view of an ultrasonic bone scalpel bit according to a first embodiment of the present disclosure.
Figure 2:
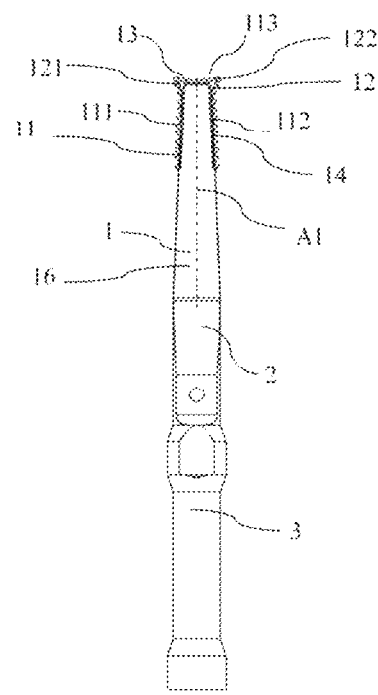
FIG. 2 is a front view of the ultrasonic bone scalpel bit according to the first embodiment of the present disclosure.

FIGS. 1 to 3C show an ultrasonic bone scalpel bit according to a first embodiment of the present disclosure. FIG. 1 is a perspective view of the ultrasonic bone scalpel bit according to the first embodiment of the present disclosure; FIG. 2 is a front view of the ultrasonic bone scalpel bit according to the first embodiment of the present disclosure; and FIG. 3A is a partially enlarged front view of a scalpel bit end portion of the ultrasonic bone scalpel bit according to the first embodiment of the present disclosure. As shown in FIGS. 1 and 2, the ultrasonic bone scalpel bit according to the first embodiment of the present disclosure includes a scalpel bit end portion 1. The scalpel bit end portion 1 is of a flat shape, specifically a shape of a flat sheet or a flat block or a shape with a flat hexagonal cross section, and preferably a shape of a flat sheet formed of a blade portion 16, the blade portion 16 including a pair of planes which are approximately parallel to each other or form an included angle no more than 10° in a width direction of the scalpel bit end portion 1. Forming the shape of a wedge with a certain included angle facilitates coolant to flow toward a distal end portion 113 of the scalpel bit end portion 1 along the blade portion 16 and further facilitates achieving sufficient cooling. The scalpel bit end portion 1 is formed with a cutting portion 11 which come into contact and cut a tissue, such as a bone, during cutting, the cutting portion 11 being symmetrically arranged relative to a longitudinal axis A1 on left and right sides of the blade portion 16 in a width direction of the scalpel bit end portion 1. The cutting portion 11 has a first side portion 111 located on one side in the width direction, a second side portion 112 located on the other side in the width direction, and a distal end portion 113 located at the furthest end of the scalpel bit. Preferably, the distance between the first side portion 111 and the second side portion 112 in the width direction of the scalpel bit end portion 1 decreases toward the distal end portion 113.

Since both sides of the scalpel bit end portion 1 are provided with the cutting portion 11 in the width direction, the ultrasonic bone scalpel can perform reciprocating cutting operations in the width direction of the scalpel bit end portion 1. Further, since the distance between the first side portion 111 and the second side portion 112 of the cutting portion 11 in the width direction decreases toward the distal end portion 113, the resistance to the scalpel bit during cutting, especially during longitudinal cutting (i.e., the cutting direction is approximately parallel to the blade portion and perpendicular to the longitudinal axis A1) is small. Still further, since the first side portion 111 and the second side portion 112 of the cutting portion 11 are symmetrical in the width direction, while performing reciprocating cutting operations that a surgical robot is good at, especially when the scalpel bit is required following a planned route to perform cutting, high repetition accuracy can be achieved by means of the symmetrically arranged first side portion 111 and second side portion 112.

In addition, a plurality of protrusions 12 are formed near the distal end portion 113 of the cutting portion 11, which symmetrically project outward from the first side portion 111 and the second side portion 112 relative to the longitudinal axis A1 in the width direction of the scalpel bit end portion 1. Preferably, the protrusions 12 include a first protrusion 121 located at the junction of the distal end portion 113 and the first side portion 111, and a second protrusion 122 located at the junction of the distal end portion 113 and the second side portion 112. Further preferably, the maximum width of protrusions 12 in the width direction of the scalpel bit end portion 1 is greater than or equal to that of a tissue contact portion of the ultrasonic bone scalpel bit in the width direction of the scalpel bit end portion. For example, if the entire scalpel bit end portion 1 might enter the human tissue during the surgical operation, the entire scalpel bit end portion 1 will be regarded as the tissue contact portion. In this way, during performing a vertical cutting that surgical robots is good at, since the protrusions 12 are arranged near the distal end portion 113 and project out from the first side portion 111 and the second side portion 112 in the width direction, coolant for cooling the scalpel bit will finally reach the protrusions 12 along the blade portion 16 of the scalpel bit end portion 1, so as to guarantee cooling effect for the scalpel bit, and the contact area of the scalpel bit and the tissue to be cut is smaller, such that the resistance to the scalpel bit moving in the tissue will also decease.

Preferably, the protrusions 12 may be formed to have a hooked, trapezoidal, square, triangular, or circular arc shape, or any combination thereof. In addition, a recess 13 which is recessed toward a proximal end of the scalpel bit end portion 1 is formed at the distal end portion 113 of the cutting portion 11. Preferably, the recess 13 is symmetrically provided relative to the longitudinal axis A1 of the scalpel bit end portion 1, and the recess 13 has a constant or gradient radius of curvature. During performing a vertical cutting (i.e., a cut of which the cutting direction is approximately perpendicular to the tissue to be cut, i.e., of which the cutting direction is approximately parallel to the longitudinal axis A1) that surgical robots is good at, due to the recessed structure of the distal end portion 113 of the cutting portion 11, the contact area between the scalpel bit and a tissue to be cut, especially a tissue such as a lateral cortical bone, is reduced, and the force applied is more uniform, thereby guaranteeing higher cutting accuracy while improving the cutting efficiency. Moreover, due to the recessed structure, a certain space is formed between the distal end portion 113 and the tissue to be cut, further facilitating the inflow of the coolant and the removal of tissue fragments.

Preferably, the first protrusion 121 located on one side of the distal end portion 113, the recess 13 located in the middle of the distal end portion 113, and the second protrusion 122 located on the other side of the distal end portion 113 are smoothly and consecutively formed on the distal end portion 113. That is, a first corner constituted by the first protrusion 121 and the recess 13 and a second corner constituted by the second protrusion 122 and the recess 13 are respectively formed on a left side and a right side of the distal end of the scalpel bit end portion 1, and the first corner, the second corner and the recess 13 are smoothly and integrally formed. This further facilitate a fast inflow of the coolant. As such, it is possible to reduce the manufacturing difficulty of the scalpel bit end portion 1 and save the costs while guaranteeing the cutting accuracy and improving cooling effect.

In addition, preferably, the cutting portion 11 is provided with a toothed structure 14. Further preferably, the toothed structure 14 may be formed into a sharp tooth structure, or may be formed into a square tooth structure, or may also be formed into a hook-shaped tooth, etc. With the toothed structure 14 formed, it is possible to prevent slipping of the scalpel bit during cutting and further reduce the contact area between the cutting portion and the tissue to be cut. The toothed structure 14 may be arranged only at the first side portion 111 and the second side portion 112 of the cutting portion 11, or may be arranged only at the distal end portion 113 of the cutting portion 11, and further preferably, the toothed structure 14 may be arranged all over the cutting portion 11.

Figure 3A:
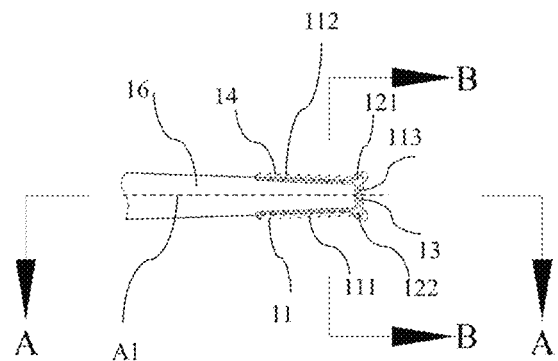
FIG. 3A is a partially enlarged front view of a scalpel bit end portion of the ultrasonic bone scalpel bit according to the first embodiment of the present disclosure.
Figure 3B:
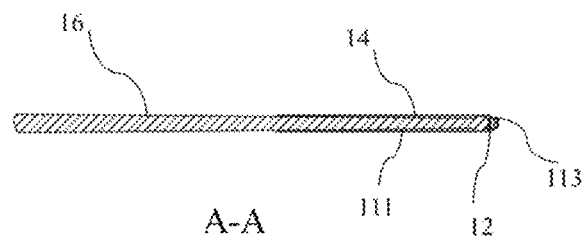
FIG. 3B is a sectional view taken along A-A in FIG. 3A.
Figure 3C:
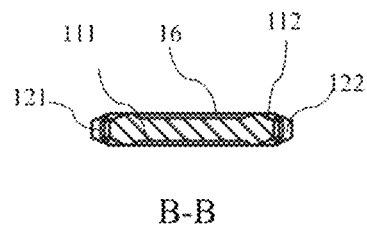
FIG. 3C is a sectional view taken along B-B in FIG. 3A.

In addition, preferably, the cutting portion 11 may be formed such that the thickness of at least part of at least one of the first side portion 111, the second side portion 112, the distal end portion 113 and the protrusions 12 is greater than that of a non-cutting portion adjacent thereto, for example, a blade portion 16, on the scalpel bit end portion 1. Preferably, as shown in FIGS. 3B and 3C, the thicknesses of the first side portion 111, the second side portion 112, the distal end portion 113 and the protrusions 12 are all greater than that of the non-cutting portion adjacent thereto. Further preferably, the thickness of the cutting portion 11 is greater than or equal to the maximum thickness of the tissue contact portion of the ultrasonic bone scalpel bit. Alternatively, at least one of the first side portion 111, the second side portion 112, the distal end portion 113 and the protrusions 12 of the cutting portion 11 has a first thickness portion and a second thickness portion which are arranged alternatively and are different in thickness, the thickness of the first thickness portion being greater than that of the second thickness portion, and the thickness of the second thickness portion being greater than that of the non-cutting portion, which is adjacent to the cutting portion, of the scalpel bit end portion. On the one hand, the first thickness portion and the second thickness portion which are arranged alternatively and are different in thickness form a channel for passage of the cooling liquid, such that the cooling liquid can be directly guided to the tissue being cut so as to improve cooling effect. On the other hand, the first thickness portion and the second thickness portion arranged alternatively and different in thickness also form a channel for passage of the bone fragments generated during cutting, such that the bone fragments can be discharged more smoothly, thereby improving the cutting efficiency and cutting accuracy.

Since the cutting portion 11 has a relatively large thickness, and at least one of the first side portion 111, the second side portion 112, the recess 13 and the protrusions 12 of the cutting portion 11 is different from the blade portion 16 in thickness. Thus, the blade portion 16 and the cutting portion 11 form a structure having a height difference in the thickness direction. Therefore, during cutting, especially during vertical cutting, the coolant is finally guided to the cutting portion 11 along the blade portion 16 and in turn flows toward a tissue to be cut, which is beneficial to guarantee cooling effect. Moreover, since the thickness of the cutting portion is greater than or equal to the maximum thickness of the tissue contact portion of the ultrasonic bone scalpel bit, in this case, the contact area between the scalpel bit and a tissue to be cut is smaller, and the resistance to the scalpel bit moving in the tissue decreases.

In addition, the ultrasonic bone scalpel bit according to the first embodiment may further include a scalpel rod 2. The scalpel rod 2 is connected to the scalpel bit end portion 1 in the front, and is provided, in the rear, with a connecting mechanism connected to other parts (such as a scalpel body 3 or an ultrasonic device, etc.) of the ultrasonic bone scalpel. The ultrasonic bone scalpel bit may have an integrated structure, or may have a split-type assembled structure. Alternatively, the ultrasonic bone scalpel bit may also not have the scalpel rod 2 such that the scalpel bit end portion 1 is directly connected to other parts of the ultrasonic bone scalpel in a connection manner that may include threaded connection, snap-in fitting, clamping, etc.

Figure 4:
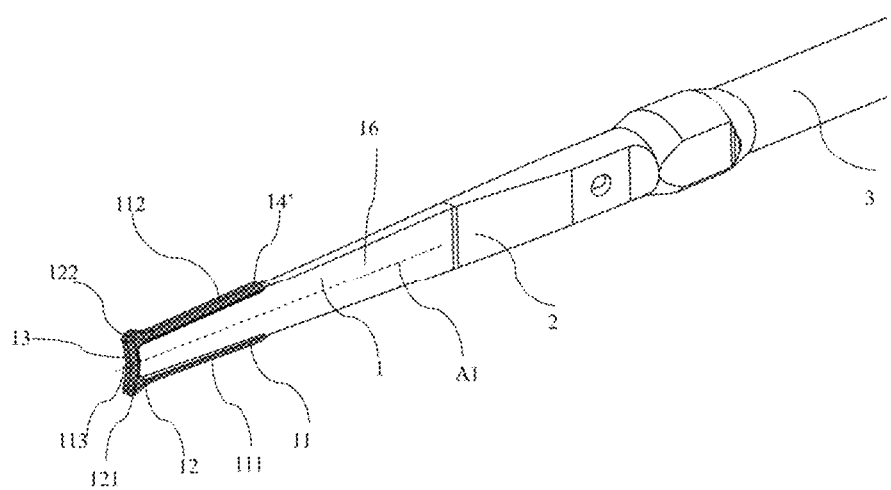
FIG. 4 is a perspective view of an ultrasonic bone scalpel bit according to a second embodiment of the present disclosure.
Figure 5:
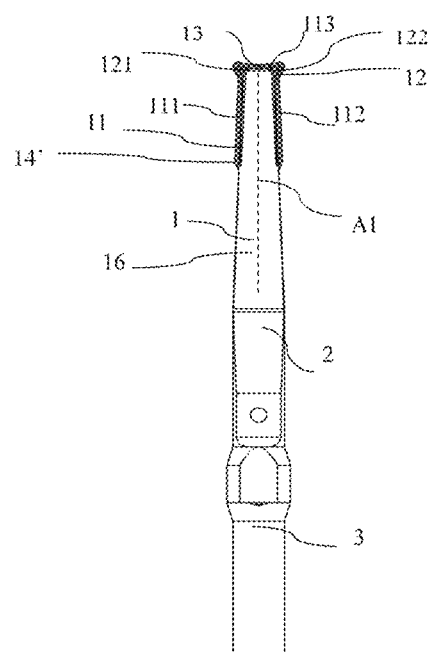
FIG. 5 is a front view of the ultrasonic bone scalpel bit according to the second embodiment of the present disclosure.

FIGS. 4 and 5 show an ultrasonic bone scalpel bit according to a second embodiment of the present disclosure. As shown in the figures, the ultrasonic bone scalpel bit according to the second embodiment of the present disclosure is substantially the same as the ultrasonic bone scalpel bit according to the first embodiment of the present disclosure, except that the cutting portion 11 of the scalpel bit end portion 1 is provided with a knurled structure 14'. Preferably, the knurled structure 14' may be arranged at the distal end of the scalpel bit end portion 1 and all over the cutting portion 11. Moreover, the knurled structure 14' may be arranged together with the toothed structure 14 on different sites the cutting portion 11. Similar to the toothed structure 14, the knurled structure 14' can prevent slipping during cutting, and can reduce the contact area of the scalpel bit end portion 1 with the tissue to be cut, thereby improving cutting efficiency. Furthermore, the knurled structure 14' is also easy to process.

Figure 6:
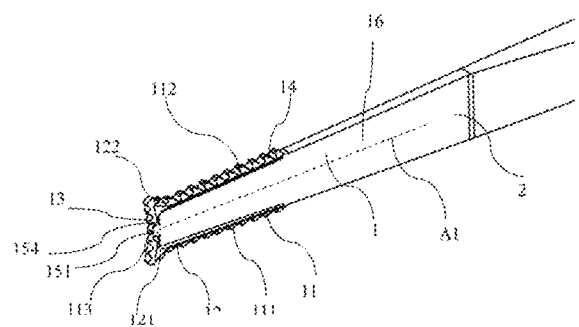
FIG. 6 is a perspective view of a scalpel bit end portion of an ultrasonic bone scalpel bit according to a third embodiment of the present disclosure.
Figure 7:
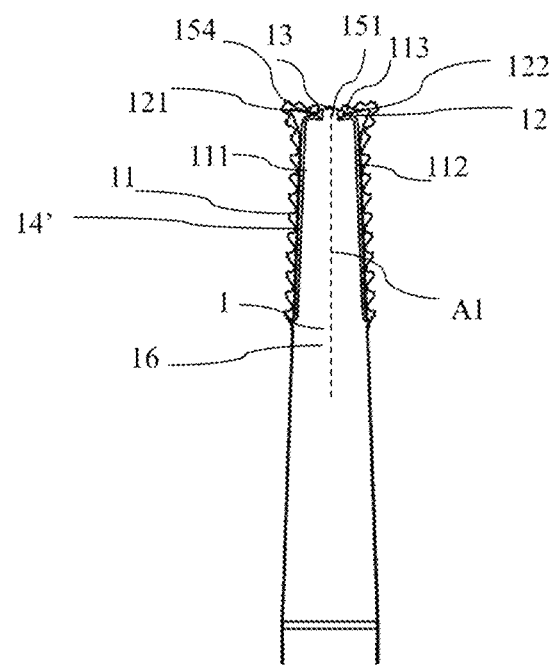
FIG. 7 is a front view of the scalpel bit end portion of the ultrasonic bone scalpel bit according to the third embodiment of the present disclosure.
Figure 8:
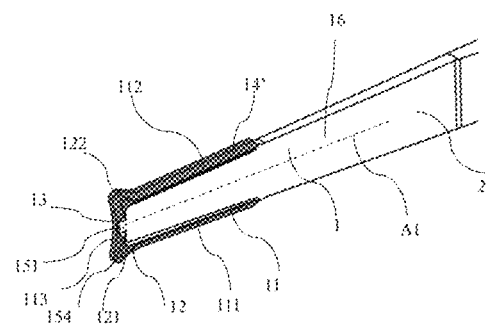
FIG. 8 is a perspective view of a scalpel bit end portion of an ultrasonic bone scalpel bit according to a fourth embodiment of the present disclosure.
Figure 9:
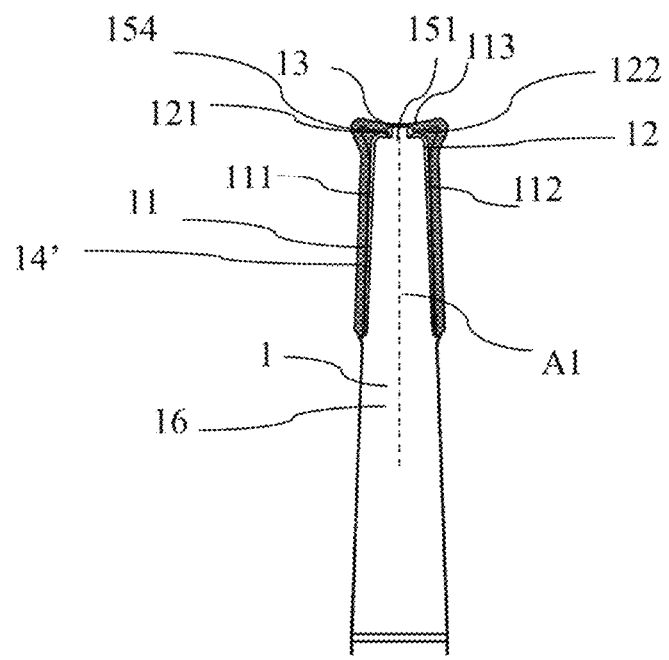
FIG. 9 is a front view of the scalpel bit end portion of the ultrasonic bone scalpel bit according to the fourth embodiment of the present disclosure.

FIGS. 6 and 7 show an ultrasonic bone scalpel bit according to a third embodiment of the present disclosure, and FIGS. 8 and 9 show an ultrasonic bone scalpel bit according to a fourth embodiment of the present disclosure. In comparison with the ultrasonic bone scalpel bit according to the first embodiment of the present invention, the ultrasonic bone scalpel bit according to the third embodiment of the present disclosure is provided with at least one guide groove formed on the scalpel bit for guiding liquid to the cutting portion 11 so as to further smoothly guide the coolant. FIGS. 6 to 9 show a guide groove 151. The guide groove 151 extends from the cutting portion 11 to the blade portion 16 on at least one side. In this way, when the ultrasonic bone scalpel bit performs cutting, especially vertical cutting, the coolant from other mechanisms of the ultrasonic bone scalpel flows to the blade portion 16 under the action of gravity, is then guided to the guide groove 151, and finally flows toward the cutting portion 11 along the guide groove 151. Therefore, the flow route of the coolant is optimized, further guaranteeing cooling effects for the scalpel bit. The fourth embodiment is substantially the same as the third embodiment, except that the cutting portion 11 of the scalpel bit end portion 1 is provided with the knurled structure 14'.

Alternatively, the guide groove 151 may have a structure of a groove that is formed only on the cutting portion 11 and is connected to the blade portion 16. In other words, it is not necessary to make a groove on the blade portion 16, but only the guide groove 151 extending to the blade portion 16 is formed on the cutting portion 11, such that the liquid guiding function is achieved by means of the height difference in the thickness direction between the cutting portion 11, the bottom of the guide groove 151 on the cutting portion 11, and the part of the blade portion 16 connected to the guide groove 151. In this way, the guide groove 151 can be formed without separately forming a grooved structure on the blade portion 16, so as to simplify the processing and reduce the cost while achieving the liquid guiding effect. It should be understood that, in addition to the function of guiding the cooling liquid, the guide groove 151 described above can also guide the bone fragments generated during cutting from the part being cut to the blade portion 16 such that the bone fragments can be flushed out by the cooling liquid or drawn out by means of an additionally provided suction device, thereby improving the cutting efficiency and cutting accuracy.

In addition, the ultrasonic bone scalpel bit can also be formed with a through hole 154 that penetrates the scalpel bit end portion in the thickness direction, and the through hole 154 may be located at a groove portion of the guide groove 151 or at a side thereof. As shown in FIGS. 6 to 9, when coolant flows along the guide groove 151, the coolant can flow out via the through hole 154 extending from the guide groove 151 to the cutting portion 11 and directly reach the tissue to be cut, thereby further enhancing the flowing of the coolant, enhancing cooling effect, and also facilitating discharge of tissue fragments.

Figure 10:
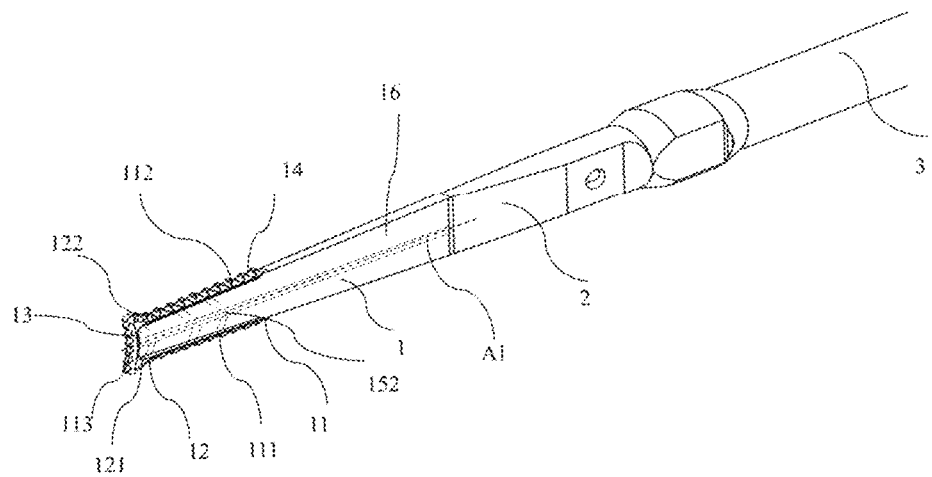
FIG. 10 is a perspective view of a scalpel bit end portion of an ultrasonic bone scalpel bit according to a fifth embodiment of the present disclosure.

FIG. 10 is a perspective view of a scalpel bit end portion of an ultrasonic bone scalpel bit according to a fifth embodiment of the present disclosure. The ultrasonic bone scalpel bit according to the fifth embodiment of the present disclosure is substantially the same as the ultrasonic bone scalpel bit according to the first to fourth embodiments of the present disclosure, except for the specific structure of a guide groove 152 arranged at the scalpel bit end portion 1. Specifically, the guide groove 152 is arranged on the blade portion 16 and extends to the first side portion 111, the second side portion 112, the recess 13 and the protrusions 12 of the cutting portion 11. Providing a groove portion on the blade portion 16 enables the coolant be guided to the corresponding part on the cutting portion 11 along a specified route more quickly, so as to guide the coolant to multiple different positions of the cutting portion 11 via the guide groove 152, thereby further guaranteeing cooling effects. The groove portion on the blade portion 16 can be formed by means of grooving or knurling.

Figure 11:
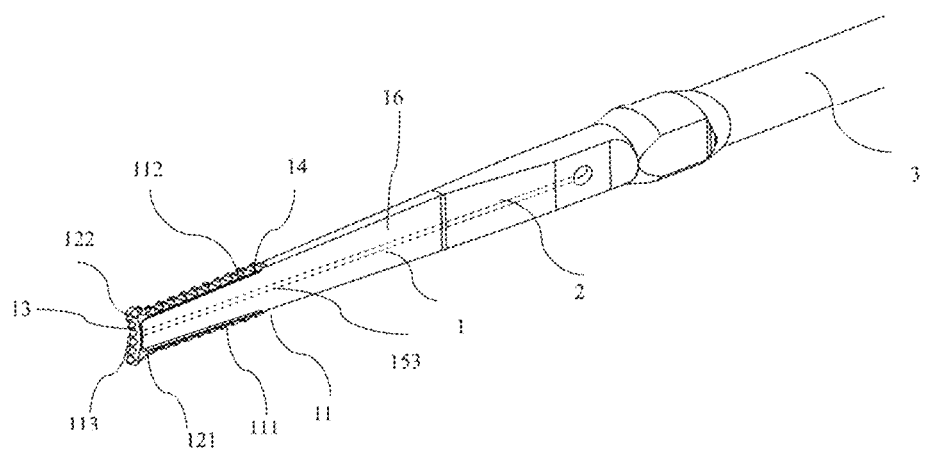
FIG. 11 is a perspective view of an ultrasonic bone scalpel bit according to a sixth embodiment of the present disclosure.

FIG. 11 shows an ultrasonic bone scalpel bit according to a sixth embodiment of the present disclosure, and FIG. 11 is a perspective view showing the structure of the ultrasonic bone scalpel bit according to the sixth embodiment of the present disclosure. The ultrasonic bone scalpel bit according to the sixth embodiment is formed to have a structure in which the scalpel bit end portion 1 has a certain thickness, and the scalpel bit end portion 1 is internally formed with a liquid flow hole 153 extending to the distal end portion 113 in the length direction of the scalpel bit end portion 1. The liquid flow hole 153 can not only guide the coolant to cool a tissue to be cut, and the tissue fragments of the tissue to be cut can also be drawn out through the liquid flow hole.

By means of using the ultrasonic bone scalpel bit according to the embodiments described above, the problems caused by inflexibility of surgical robots can be avoided, and the advantages of surgical robots in terms of speed, force control, and repetition accuracy control are fully utilized, which improves the efficiency of surgery and can further improve cooling effect.

Figure 12:
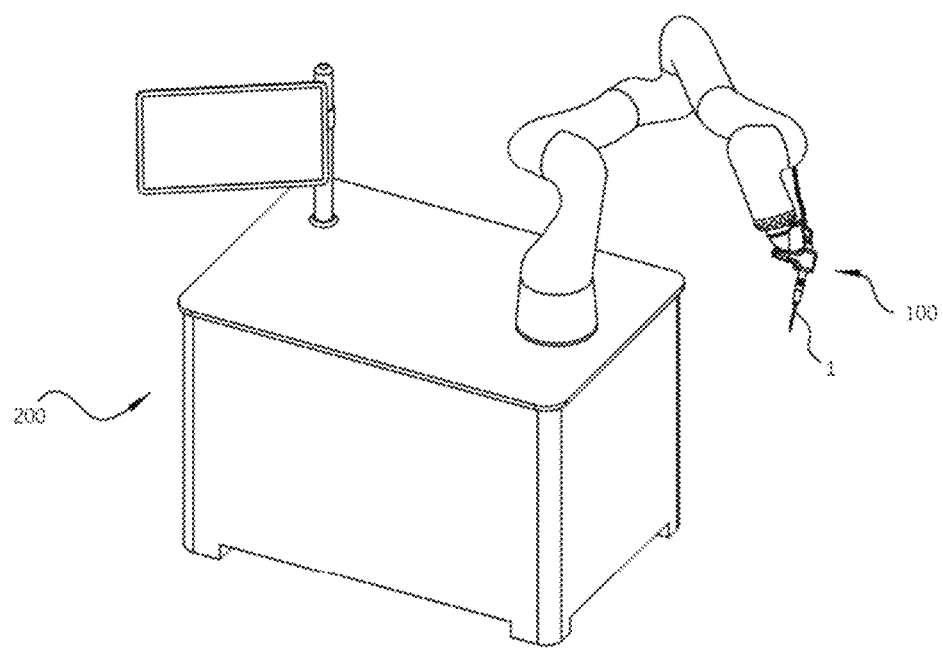
FIG. 12 is a schematic view of a robot-assisted ultrasonic bone power system according to the present disclosure.

The present disclosure further provides a robot-assisted ultrasonic bone power system. As shown in FIG. 12, the robot-assisted ultrasonic bone power system includes an ultrasonic transducer for converting electric energy into mechanical energy, an ultrasonic bone scalpel 100 for transferring the mechanical energy to the bone to be cut, and a robot-assisted surgery system 200 for assisting in a surgical operation, the ultrasonic bone scalpel of the robot-assisted ultrasonic bone power system using the ultrasonic bone scalpel bit according to any one of the above embodiments of the present disclosure.

Although the embodiments or examples of the present disclosure have been described with reference to the drawings, it should be understood that the methods, systems and devices described above are merely exemplary embodiments or examples, and the scope of the present disclosure is not limited by the embodiments or examples, and is only defined by the scope of the granted claims and the equivalents thereof. Various elements in the embodiments or examples may be omitted or substituted by equivalent elements thereof. Further, the above embodiments, examples and various key elements therein can be appropriately combined in various ways according to the specific structures. It is important that, as the technology evolves, many elements described herein may be replaced with equivalent elements that appear after the present disclosure.

The invention claimed is:

1. An ultrasonic bone scalpel bit, including a scalpel bit end portion located at a distal end of the scalpel bit, the scalpel bit end portion being formed to have a flat shape and provided with a cutting portion, wherein the cutting portion includes a distal end portion, a first side portion and a second side portion, the first side portion and the second side portion being symmetrically arranged relative to a longitudinal axis of the scalpel bit end portion in a width direction of the scalpel bit end portion, wherein the distance between the first side portion and the second side portion in a width direction of the scalpel bit end portion decreases or remains unchanged toward the distal end portion;

the cutting portion further includes a plurality of protrusions formed near the distal end portion, the plurality of protrusions projecting outwardly from the first side portion and the second side portion symmetrically relative to the longitudinal axis in the width direction of the scalpel bit end portion;

and wherein the plurality of protrusions include a first protrusion and a second protrusion, the first protrusion is located at the junction of the distal end portion and the first side portion, and the second protrusion is located at the junction of the distal end portion and the second side portion; and wherein the maximum width of the first protrusion and the second protrusion in the width direction of the scalpel bit end portion is greater than that of a tissue contact portion of the ultrasonic bone scalpel bit in the width direction of the scalpel bit end portion the maximum distance between the first side portion and the second side portion in a width direction of the scalpel bit end portion; and a recess which is recessed toward a proximal end of the scalpel bit end portion is formed on the distal end portion.

2. The ultrasonic bone scalpel bit of claim 1, wherein the recess is symmetrically provided relative to the longitudinal axis of the scalpel bit end portion.

3. The ultrasonic bone scalpel bit of claim 1, wherein the recess has a constant or gradient radius of curvature.

4. The ultrasonic bone scalpel bit of claim 1, wherein the first protrusion, the recess and the second protrusion are smoothly and consecutively formed.

5. The ultrasonic bone scalpel bit of claim 1, wherein the thickness of at least part of at least one of the distal end portion, the first side portion, the second side portion and the protrusions of the cutting portion is greater than that of a non-cutting portion, which is adjacent to the cutting portion, of the scalpel bit end portion.

6. The ultrasonic bone scalpel bit of claim 5, wherein the thicknesses of the distal end portion, the first side portion, the second side portion and the protrusions of the cutting portion are greater than that of the non-cutting portion, which is adjacent to the cutting portion, of the scalpel bit end portion.

7. The ultrasonic bone scalpel bit of claim 1, wherein at least one of the distal end portion, the first side portion, the second side portion and the protrusions of the cutting portion has a first thickness portion and a second thickness portion which are arranged alternatively and are different in thickness, with the thickness of the first thickness portion being greater than that of the second thickness portion.

8. The ultrasonic bone scalpel bit of claim 7, wherein the thickness of the second thickness portion is greater than that of the non-cutting portion, which is adjacent to the cutting portion, of the scalpel bit end portion.

9. The ultrasonic bone scalpel bit of claim 1, wherein the cutting portion is at least partially provided with a toothed structure and/or a knurled structure.

10. The ultrasonic bone scalpel bit of claim 9, wherein the toothed structure and/or the knurled structure of the cutting portion is provided all over the cutting portion.

11. The ultrasonic bone scalpel bit of claim 1, wherein the protrusions have a hooked, trapezoidal, square, triangular, or circular arc shape or any combination thereof.

12. The ultrasonic bone scalpel bit of claim 1, wherein the ultrasonic bone scalpel bit is provided with at least one guide groove for guiding liquid to the cutting portion.

13. The ultrasonic bone scalpel bit of claim 12, wherein the at least one guide groove guides the liquid to at least one of the distal end portion, the first side portion, the second side portion and the protrusions of the cutting portion.

14. The ultrasonic bone scalpel bit of claim 1, wherein the ultrasonic bone scalpel bit is formed with at least one through hole that penetrates in a thickness direction of the scalpel bit end portion; and/or
wherein the ultrasonic bone scalpel bit is formed with a through hole that extends to the distal end portion in a length direction of the scalpel bit end portion in the scalpel bit end portion.

15. The ultrasonic bone scalpel bit of claim 1, wherein the ultrasonic bone scalpel bit includes a scalpel rod connected to the scalpel bit end portion, and the scalpel bit end portion and the scalpel rod are integrally formed.

16. The ultrasonic bone scalpel bit of claim 1, wherein the thickness of the cutting portion is greater than or equal to the maximum thickness of the tissue contact portion of the ultrasonic bone scalpel bit.

17. A robot-assisted ultrasonic bone power system, including an ultrasonic bone power system and a robot-assisted surgery system, wherein the ultrasonic bone power system includes:
an ultrasonic transducer for converting electric energy into mechanical energy;
an ultrasonic bone scalpel for transferring the mechanical energy to a bone to be cut; and
the robot-assisted surgery system for assisting in a surgical operation,
wherein the ultrasonic bone scalpel has an ultrasonic bone scalpel bit including a scalpel bit end portion located at a distal end of the scalpel bit, the scalpel bit end portion being formed to have a flat shape and provided with a cutting portion, wherein
the cutting portion includes a distal end portion, a first side portion and a second side portion, the first side portion and the second side portion being symmetrically arranged relative to a longitudinal axis of the scalpel bit end portion in a width direction of the scalpel bit end portion, wherein the distance between the first side portion and the second side portion in a width direction of the scalpel bit end portion decreases or remains unchanged toward the distal end portion;
the cutting portion further includes a plurality of protrusions formed near the distal end portion, the plurality of protrusions projecting outwardly from the first side portion and the second side portion symmetrically relative to the longitudinal axis in the width direction of the scalpel bit end portion; and wherein the plurality of protrusions include a first protrusion and a second protrusion, the first protrusion is located at the junction of the distal end portion and the first side portion, and the second protrusion is located at the junction of the distal end portion and the second side portion; and wherein the maximum width of the first protrusion and the second protrusion in the width direction of the scalpel bit end portion is greater than the maximum distance between the first side portion and the second side portion in a width direction of the scalpel bit end portion; and
a recess which is recessed toward a proximal end of the scalpel bit end portion is formed on the distal end portion.

* * * * *